United States Patent [19]

Dailey

[11] Patent Number: 5,343,634
[45] Date of Patent: Sep. 6, 1994

[54] OSTOMY POUCH DRYING CONTAINER

[76] Inventor: Carol A. Dailey, 476 Jeffreys Dr., Elizabeth, Pa. 15037

[21] Appl. No.: 156,303

[22] Filed: Nov. 23, 1993

[51] Int. Cl.⁵ .............................................. F26B 25/00
[52] U.S. Cl. ...................................... 34/104; 34/202; 34/621
[58] Field of Search ...................... 34/151, 90, 91, 104, 34/105, 106, 21, 201, 202, 218, 22, 23; 604/332

[56] References Cited

U.S. PATENT DOCUMENTS

| | | | |
|---|---|---|---|
| 2,156,784 | 5/1939 | Jensen | 34/26 |
| 2,253,475 | 8/1941 | Willber | 312/151 |
| 2,850,810 | 9/1958 | Lyons, III et al. | 34/163 |
| 3,059,345 | 10/1962 | Kaufman | 34/80 |
| 3,280,477 | 10/1966 | Rawlins | 34/151 |
| 3,798,788 | 3/1974 | Kuntz | 34/104 |
| 4,642,106 | 2/1987 | Downey | 604/332 |
| 5,022,693 | 6/1991 | Loveless | 294/1.1 |

*Primary Examiner*—Denise Gromada
*Attorney, Agent, or Firm*—Webb Ziesenheim Bruening Logsdon Orkin & Hanson

[57] ABSTRACT

An apparatus for drying an ostomy pouch in a discreet manner includes a container having a box-shaped structure formed from top, bottom, front, back and side panels with an L-shaped extensor rod extending from an inner surface of one of the back or side panels. At least two of the front, side and top panels include a plurality of perforations therethrough to allow air flow through the container to aid in drying an ostomy pouch mounted on the extensor rod. The front panel is moveable from a closed position adjacent the top, bottom and side panels to an open position to allow access to an interior region of the box-shaped structure and to the extensor rod. A removable drip pan can be included for convenient collection and removal of all drainage from the ostomy pouch.

20 Claims, 5 Drawing Sheets

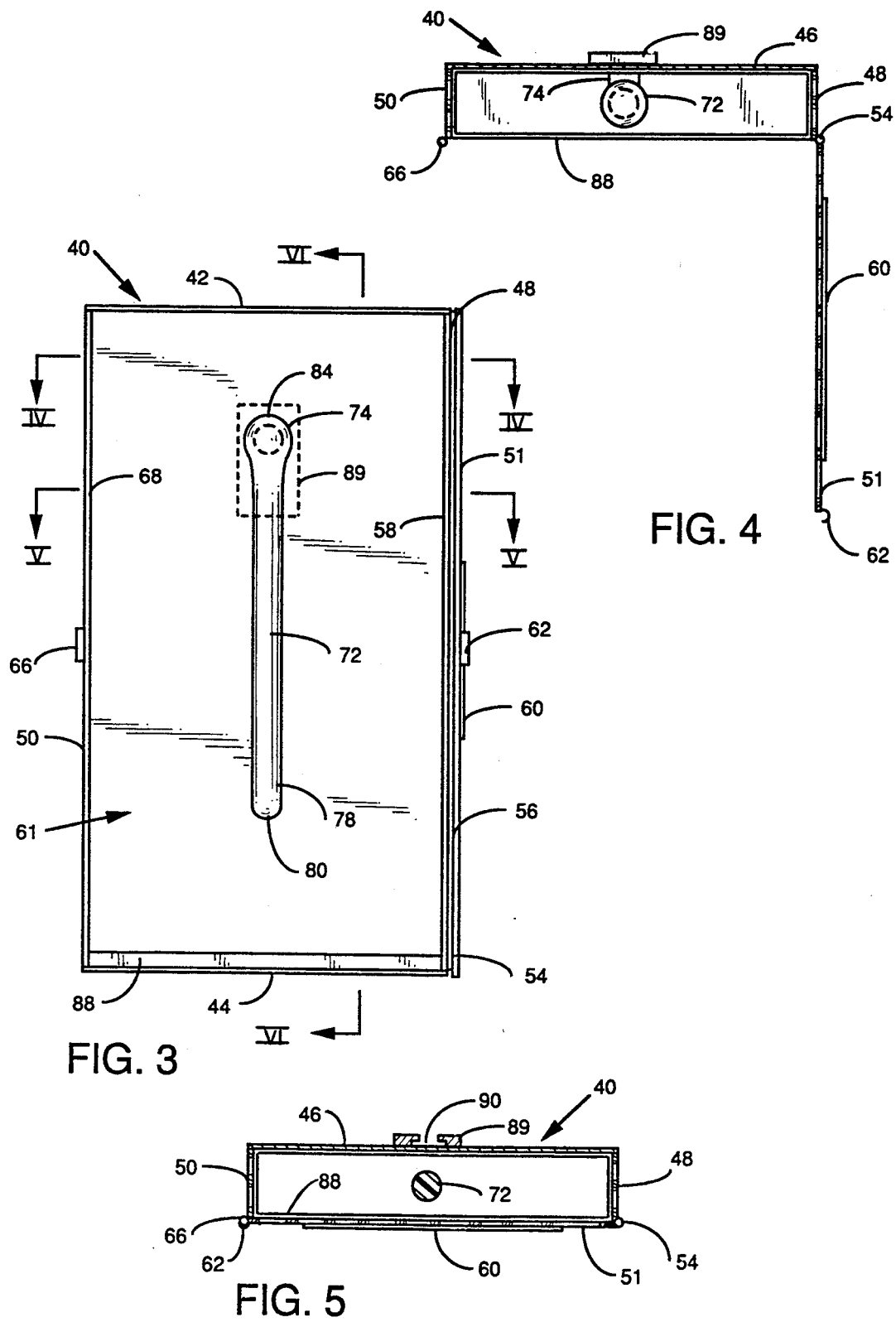

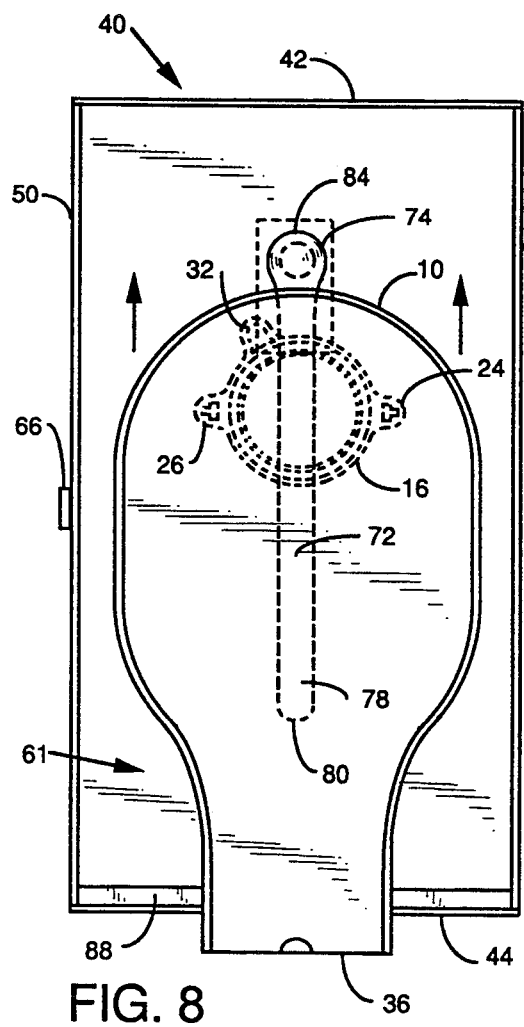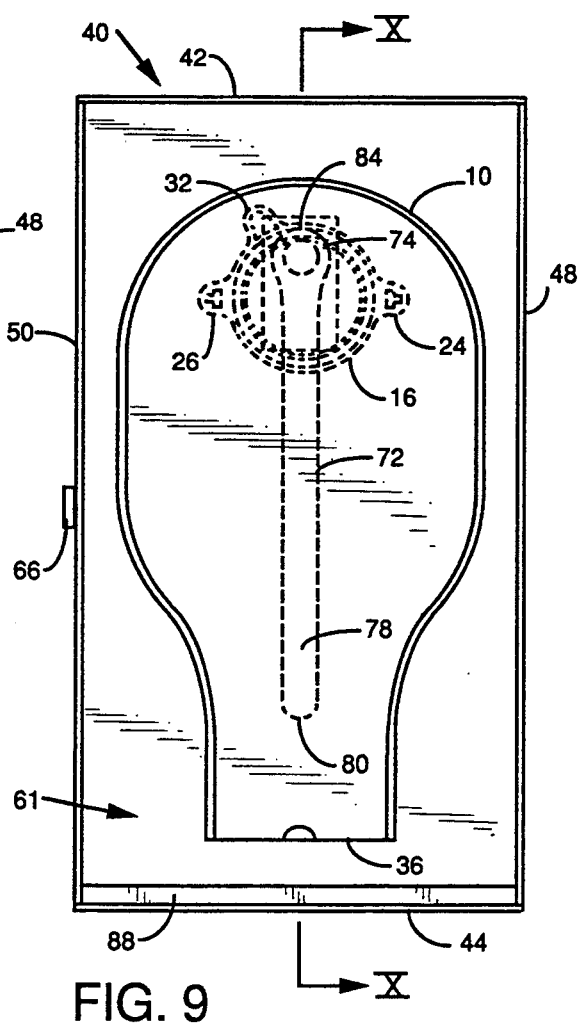

OSTOMY POUCH DRYING CONTAINER

BACKGROUND OF THE INVENTION

1. Field of the Invention

This invention relates to the drying of ostomy pouches and, more particularly, to an apparatus for effectively drying ostomy pouches in a discreet manner.

2. Background of the Prior Art

In the United States, a considerable number of people have undergone a surgical procedure generally referred to as an ostomy, and many more ostomy surgeries are performed each year. In procedures of this type, a surgeon brings a portion of the colon or other body member through a surgically created opening in the abdominal wall. This opening forms a stoma, or mouth, whose edges are sutured to the patient's skin. The stoma has no sphincter muscle, and thus, cannot be voluntarily opened and closed by the patient. This requires that a collection pouch or bag be worn by the patient to receive bodily discharges and to retain the discharges until the pouch can be removed and cleaned or replaced. As with many so-called convenience products, disposable ostomy pouches can become expensive when a long-term use is contemplated. Thus, the typical ostomy patient will use an ostomy pouch which can be cleaned and reused.

Used ostomy pouches must be handled carefully to avoid infection or the spread of disease caused by microorganisms, such as bacteria. Microorganisms thrive in the moist, nutrient-rich environment of human waste contained within a used ostomy pouch. To ensure that precautions are taken, various governmental agencies strictly regulate the handling and disposal of products that have come into contact with human waste. These precautions are likely to become more burdensome as the use of ostomy pouches increases.

Ostomy pouches are generally well-known in the art and are commercially available from several manufacturers. FIG. 1 is a view of an ostomy pouch sold by E. R. Squibb and Sons, Inc. under the name ConvaTec ®. The ostomy pouch 10 has a hollow, flexible body 12 formed of an inert, flexible material. A raised and resilient mouth rim 16 is joined to a front wall 18 of the ostomy pouch 10. The mouth rim 16 surrounds an opening 20 communicating with an interior 22 of the ostomy pouch 10. The mouth rim 16 is shaped to be snap fit about a stoma flange (not shown) that is adhesively attached to the skin around the stoma of the ostomy patient. The mouth rim 16 includes a pair of peripherally spaced, belt engageable tabs 24 and 26 which have apertures 28 and 30, respectively, therein. The belt engageable tabs 24 and 26 are used to help secure the ostomy pouch 10 to a patient. The mouth rim 16 of the ostomy pouch 10 includes a grip tab 32 which can be grasped by the ostomy patient or an attendant when removing and/or attaching the ostomy pouch 10. The ostomy pouch 10 also has a tail portion 34 which terminates in a discharge opening 36 communicating with the interior 22 of the flexible body 12. The tail portion 34 is typically closed by rolling it up and securing it in place by a removable clip assembly (not shown).

Before cleaning the ostomy pouch 10, the mouth rim 16 must be removed from the stoma flange. Once the mouth rim 16 has been removed from the stoma flange, the clip assembly is removed and the tail portion 34 is opened allowing the contents of the ostomy pouch 10 to be emptied into a suitable receptacle, such as a toilet. The emptied ostomy pouch 10 must then be thoroughly rinsed and soaked to ensure that it is completely clean for reuse. A small amount of water commonly remains in the ostomy pouch 10 after a thorough cleaning and rinsing of its interior 22. Cleaned ostomy pouches must, therefore, be dried completely to avoid the growth of microorganisms in the residual moist environment of the ostomy pouch interior 22.

Drying of the ostomy pouch interior 22 is commonly effected by placing the ostomy pouch 10 on or near the edge of a receptacle, such as a bathtub, a sink, or a commode, with the tail portion 34 extended downwardly slightly into the receptacle. Drainage then occurs as the residual moisture drips into the receptacle. Often this drying procedure results in the ostomy pouch 10 being in full view of anyone visiting a patient and can be a particular problem in a hospital room. The visible draining ostomy pouch 10 is unsightly and serves to potentially embarrass the patient before friends or visitors.

The prior art has proposed several devices for draining and evacuating the contents of ostomy pouches. For example, U.S. Pat. No. 5,022,693 to Loveless discloses an ostomy pouch holder which permits the pouch to be easily manipulated during emptying and then retained securely in a toilet during cleaning. U.S. Pat. No. 4,642,106 to Downey discloses an implement for forcibly emptying the contents of an ostomy pouch prior to cleaning. However, the prior art has not provided a solution to the problems of drying ostomy pouches in a hygienically acceptable, discreet manner once the ostomy pouches have been emptied and cleaned.

Thus, it is an object of the present invention to provide a means of drying the ostomy pouch discreetly, out of the plain view of one visiting the patient, and to minimize potential embarrassment to the patient. Additionally, it is an object of the present invention to provide a highly effective means of drying an ostomy pouch. It is also an object of this invention to provide a sanitary means for collecting and removing any discharge from a cleaned ostomy pouch.

SUMMARY OF THE INVENTION

Accordingly, I have invented an apparatus for hygienically and effectively drying an ostomy pouch in a discreet manner to avoid an unsightly appearance and possible embarrassment to a patient. The apparatus has a plurality of panels, including a top panel, a bottom panel, a back panel and a pair of side panels which are joined together along adjacent outer edges to form a hollow, box-shaped structure. The apparatus also includes a front panel attached to one of the bottom, top and side panels, preferably connected by at least one hinge along a first vertical edge to one of the side panels. The front panel is moveable from a closed position adjacent the top, bottom and side panels to an open position providing access to an interior of the box-shaped structure. At least two, and preferably all four, of the top, front and side panels have a plurality of perforations therethrough to permit air to flow to the interior of the box-shaped structure. A substantially L-shaped extensor rod is positioned within the interior of the box-shaped structure. The extensor rod includes a first segment which is attached to an inner surface of one of the back and side panels, preferably the back panel, and extends substantially horizontally therefrom. The extensor rod further includes a second segment which is preferably cylindrically shaped and flexible. The second segment is attached to the first segment and extends downwardly and vertically toward the bottom panel and has a lower end which is spaced above the bottom panel. The lower end of the extensor rod is preferably round and smooth. The extensor rod also has a raised ridge on an upper surface of the extensor rod where the first and second segments are joined together. The extensor rod is configured to receive and hold an ostomy pouch thereon by passing a mouth rim of the ostomy pouch over the lower end of the second segment, along the second segment and over the raised ridge with the mouth rim resting securely on the first segment behind the raised ridge. The ostomy pouch hangs along and is held open by the extensor rod, permitting the ostomy pouch to be dried.

The front panel can include a second vertical edge carrying a latch or clasping means for latching or clasping the second vertical edge to the other of the side panels. The front panel may also include a name plate holder. The back panel may include a wall mounting bracket on an outer surface thereof for fastening the box-shaped structure to a wall. A drip pan may be provided on an upper surface of the bottom panel, beneath the extensor rod and configured for collecting discharge from an ostomy pouch mounted on the extensor rod. The panels and the extensor rod may be constructed from an inert material which may be sterilized, such as a polyamide polymer, a polycarbonate, a styrene-acrylonitrile resin, or a polyethersulfone.

BRIEF DESCRIPTION OF THE DRAWINGS

FIG. 3 is a front view of the ostomy pouch drying container shown in FIG. 2, with the front panel open;

FIG. 4 is a section taken along lines IV—IV in FIG. 3;

FIG. 5 is a section taken along lines V—V in FIG. 3, but with the front panel in a closed position;

FIG. 8 is a front view of the ostomy pouch drying container shown in FIG. 2, with the front panel removed, and showing an ostomy pouch being placed on the extensor rod;

FIG. 9 is a front view, similar to FIG. 8, of the ostomy pouch drying container shown in FIG. 2 and showing an ostomy pouch positioned completely on the extensor rod;

DETAILED DESCRIPTION OF THE PREFERRED EMBODIMENTS

Figure 1:
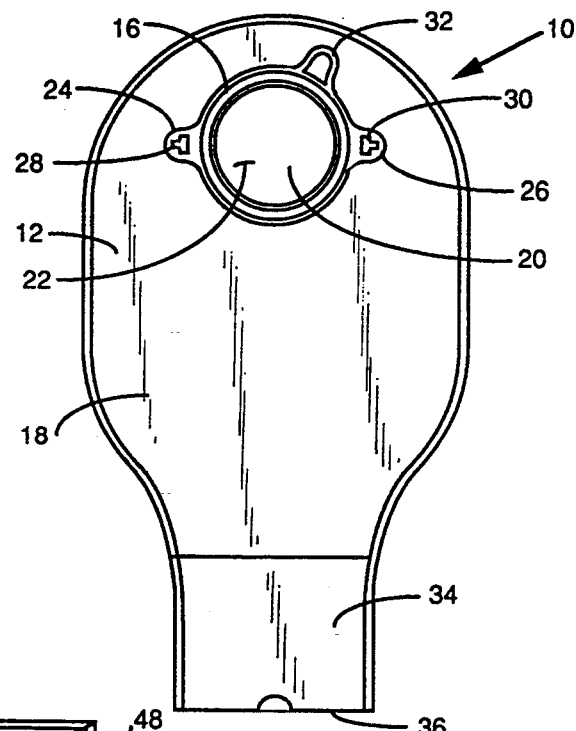
FIG. 1 is a front view of a prior art ostomy pouch.
Figure 2:
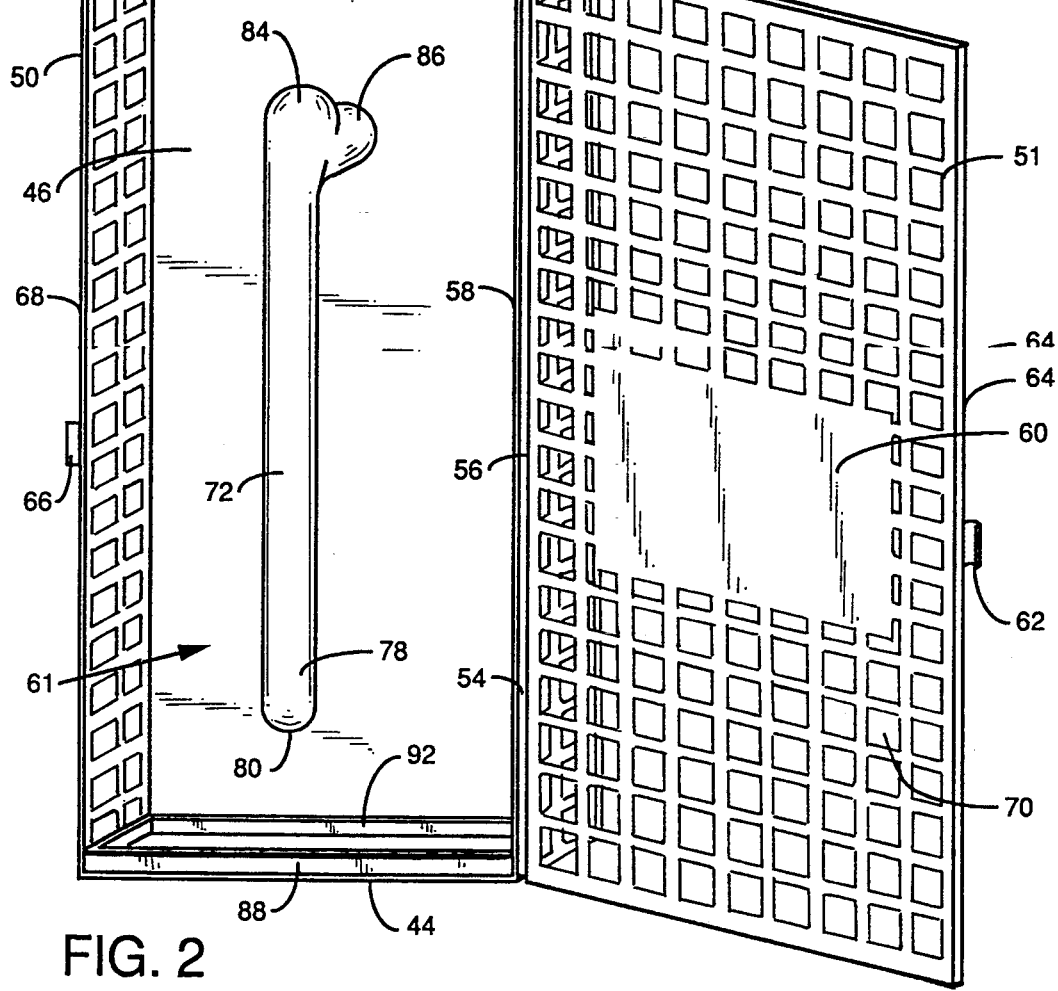
FIG. 2 is a perspective view of an ostomy pouch drying container in accordance with the present invention, with the front panel in an open position.
Figure 6:
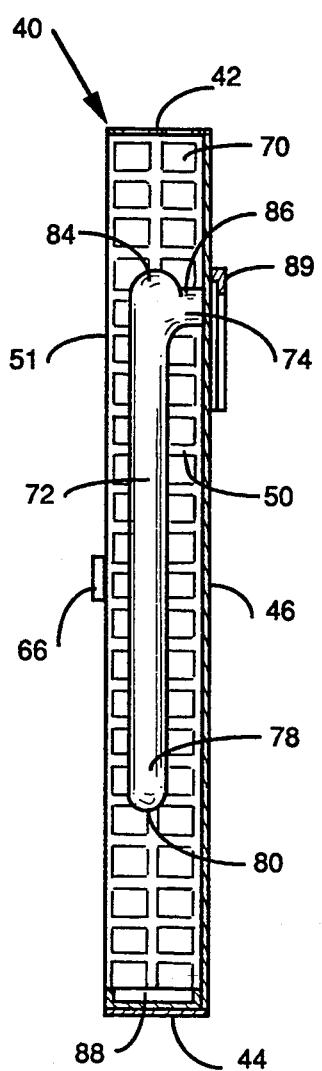
FIG. 6 is a section taken along lines VI—VI in FIG. 3.

One embodiment of an ostomy pouch drying container in accordance with the present invention is shown in FIGS. 2-7. The container 40 includes a plurality of panels, including a top panel 42, a bottom panel 44, a back panel 46 and a pair of side panels 48 and 50, joined together along adjacent outer edges to form a hollow, box-shaped structure. A front panel 51 is attached by a thin elongated seam 54 or crease which serves as a hinge between the front panel 51 and the side panel 48. The front panel 51 may also be attached by one or more individual hinges along a first vertical edge 56 of the front panel 51 and a front vertical edge 58 of side panel 48. Each of the top, bottom, back and side panels 42, 44, 46, 48 and 50 is flat and rectangular. The front panel 51 is substantially flat and rectangular, but may include a solid name plate holder 60 having a groove on an outer surface for holding a sign with the patient's name or pertinent instructions. The front panel 51 is moveable from a closed position adjacent the top panel 42, bottom panel 44, and side panels 48 and 50, to an open position providing access to an interior 61 of the box-shaped structure. The front panel 51 is locked in the closed position by a latch 62 or clasp along a second vertical edge 64 of the front panel 51 which engages a latch receiving means 66 located along a front vertical edge 68 of side panel 50. The top panel 42, front panel 51, and side panels 48, 50 have a plurality of perforations 70 therethrough to permit air to flow to the interior 61 of the box-shaped structure, and the bottom panel 44 and back panel 46 are solid in the embodiment shown in FIGS. 2-7. At least two of the top panel 42, front panel 51 and side panels 48, 50 must have a plurality of perforations 70. Although the bottom panel 44 and the back panel 46 may each also contain a plurality of perforations 70, it is preferred that these panels be solid as shown. The front panel 51 may include a plurality of perforations 70 around a provided solid name plate holder 60.

The perforations 70 may be a series of holes, grooves, slots or other known apertures as long as air flow to the interior 61 of the box-shaped structure is provided. Furthermore, it is preferred that the perforations 70 be formed in the panels such that a weaving of overlapping material strips is avoided. Rather, a substantially planar surface including the perforations 70 therein is preferred since that configuration provides for easy cleaning and sterilization while minimizing dust and dirt collection between overlapping materials.

A substantially L-shaped extensor rod 72 is positioned within the interior 61 of the box-shaped structure. The extensor rod 72 includes a first segment 74 attached to an inner surface of the back panel 46, and extending substantially horizontally therefrom. The extensor rod 72 further includes a second segment 78 attached to the first segment 74 and extending downwardly and vertically toward the bottom panel 44. The second segment 78 is preferably cylindrically shaped and constructed from a soft plastic material such that it is pliable and flexible as compared to the more rigid and stiff first segment 74. The second segment 78 further has a lower end 80, which is smooth, rounded and spaced above the bottom panel 44. The extensor rod 72 also includes a raised ridge 84 on an upper surface 86 thereof where the first segment 74 and second segment 78 are joined together.

The present invention can also include an open-topped drip pan 88 which is carried on an upper surface of the bottom panel 44, beneath the lower end 80 of the extensor rod 72. The drip pan 88 is rectangular in shape and has upwardly extending side walls 92. The drip pan 88 is also dimensioned so that it can be inserted or removed from the container 40 without tipping or tilting the drip pan 88. Although a variety of dimensions for both the container 40 and the drip pan 88 may be employed, a drip pan 88 having a height of one (1) inch, width of seven (7) inches, and depth of one and one-half (1.5) inches and a container 40 having a height of fifteen (15) inches, width of eight (8) inches, and depth of two (2) inches would appear to be suitable for standard ostomy pouches.

Figure 7:
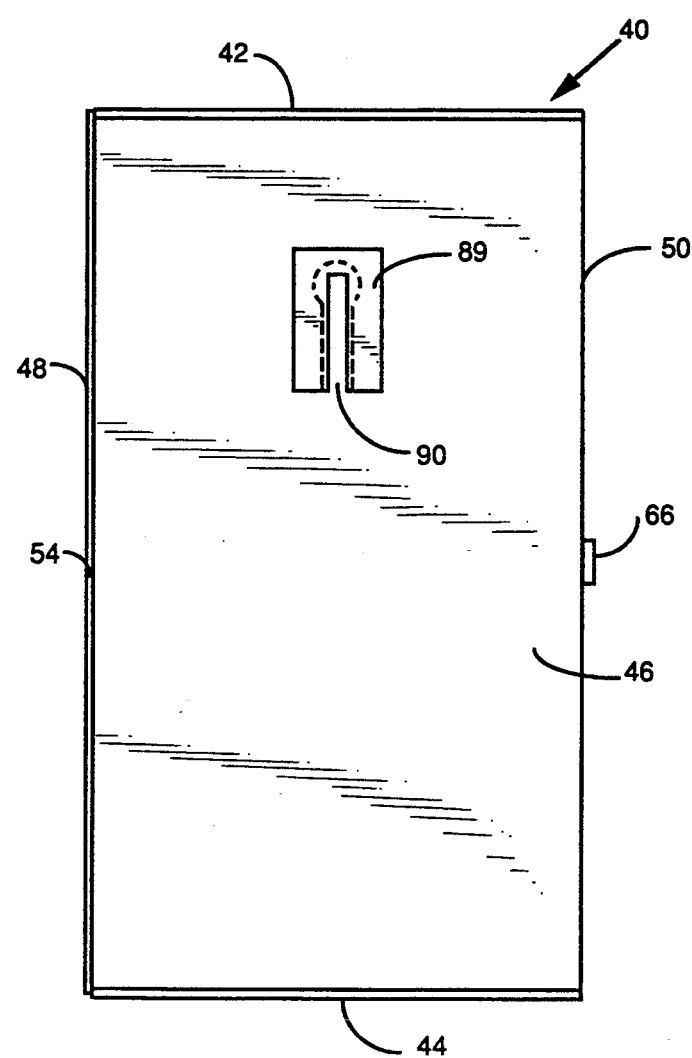
FIG. 7 is a back view of the ostomy pouch drying container shown in FIG. 2.

The ostomy pouch drying container 40 of the present invention may be free standing or it may be attached to a support structure by a variety of fastening means. As shown in FIG. 7, the outer surface of the back panel 46 carries a wall mounting bracket 89 having a slot 90 engageable with a mounting post which is mounted on and projects from a wall. The container 40 can thus be slipped onto the wall post and easily removed when it is not in use or when cleaning or sterilization is needed.

A variety of means may be used to attach the bottom panel 44, back panel 46, side panels 48, 50 and top panel 42 together as described above and in attaching the extensor rod 72 to the back panel 46. Conventional nails, screws and tongue and groove arrangements can be used alone or in combination with adhesive materials or glues. The front panel 51 may also be attached to one or more of the top panel 42, bottom panel 44 or side panels 48, 50 in a variety of ways, including a sliding door arrangement in which the front panel 51 slides along a groove or track. Additionally, the embodiment of the present invention as shown in FIGS. 2-7 uses an elongated seam 54 which serves as a hinge and which allows the front panel 51 to move in a door-like fashion in relation to side panel 48. An alternative embodiment utilizing one or more hinges connected to a first vertical edge 56 of the front panel 51 and a front vertical edge 58 of side panel 48 is equally suitable.

The extensor rod 72, panels 42, 44, 46, 48, 50, 51 and drip pan 88 are preferably made from an inert material which may be cleaned with soap and water and either gas or steam sterilized. The material is preferably selected from polyamide polymers, polycarbonates, styrene-acrylonitrile resins, and polyethersulfones, all of which are believed to be suitable for repeated sterilizations.

Figure 10:
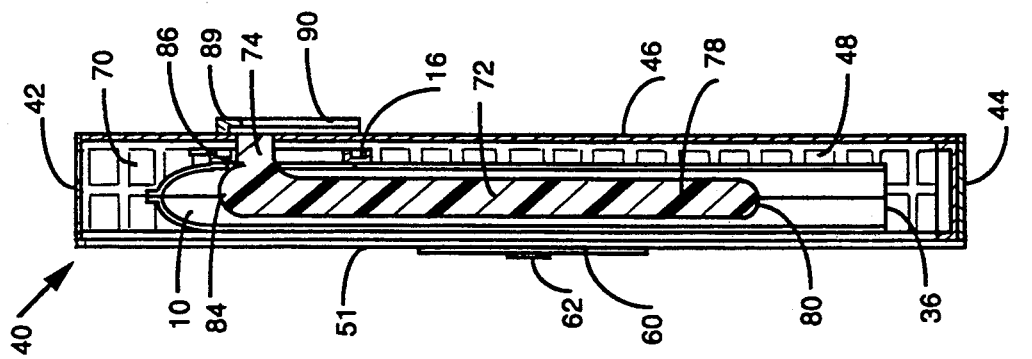
FIG. 10 is a section taken along lines X—X in FIG. 9, with the front panel closed.

FIGS. 8-10 show how an ostomy pouch 10 is dried with the present invention. With the front panel 42 open, the mouth rim 16 of the ostomy pouch 10 is placed around the lower end 80 of the extensor rod 72, without contacting the bottom panel 44 or drip pan 88, and is pulled up around the flexible second segment 78 of the extensor rod 72. This position is shown in FIG. 8. The mouth rim 16 is then further pulled up and over the raised ridge 84 to a secured position on the first segment 74 of the extensor rod 72 as shown in FIGS. 9 and 10. The bulk of the ostomy pouch 10 covers the second segment 78 of the extensor rod 72. The raised ridge 84 prevents the ostomy pouch 10 from slipping off of the extensor rod 72. Furthermore, the length of the extensor rod 72 and the angle at which the first segment 74 and second segment 78 intersect force the ostomy pouch 10 into an open position which facilitates drainage and air flow therethrough. Once the ostomy pouch 10 is securely in place on the extensor rod 72, the front panel 51 is closed to conceal the drying ostomy pouch 10 from plain view. Once dry, the ostomy pouch 10 can be easily removed by opening the front panel 51 and slipping the ostomy pouch 10 from the extensor rod 72 in the reverse manner from which it was placed thereon. Care should be taken to prevent the ostomy pouch 10 from contacting any drainage which may be contained within the drip pan 88. The drip pan 88 can be removed from the container 40 prior to removing the ostomy pouch 10 from the extensor rod 72.

Figure 11:
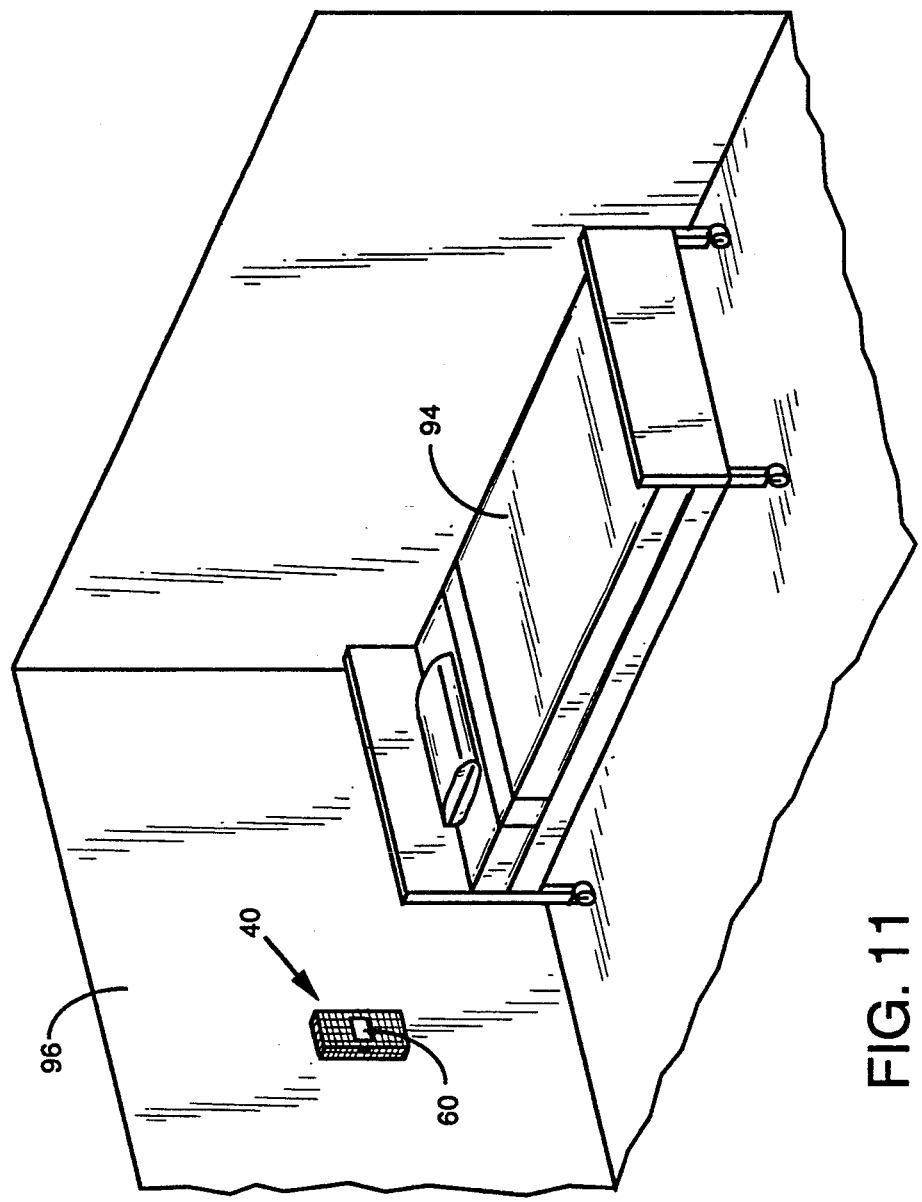
FIG. 11 is a perspective view of a hospital room showing the ostomy pouch drying container of FIG. 2 placed near a patient's bed.

As shown in FIG. 11, a patient's bed 94 is positioned near a wall 96 in a typical hospital room. The container 40 can be affixed to the wall 96 by the engagement of a wall mounting bracket 89 on the outer surface of the back panel 46 and the post (not shown) mounted on the wall 96. The container 40 can be located close to the bed 94 allowing a person caring for the patient convenient access to the container 40 as shown, but is preferably located in a bathroom. The container 40 is also positioned such that a person who is standing or sitting on an object equal in height with the bed 94 can easily reach and use the container 40. The container 40 also presents an appropriate appearance in a hospital room or other health care facility. The container 40 can be assigned to a room of a patient using an ostomy pouch 10 and then removed when no longer needed.

The present invention has many advantages, including providing effective drying of an ostomy pouch 10. The shape of the extensor rod 72, in particular, allows the ostomy pouch 10 to be held open and to facilitate drainage and drying of the interior 22 of the ostomy pouch 10. Furthermore, the container 40 is designed to provide easy mounting on a wall 96 and is perforated to allow for sufficient air flow to an ostomy pouch 10 positioned therein. Moreover, the container 40 shields the ostomy pouch 10 from the plain view of visitors or other persons in a hospital or other room. Thus, the present invention not only has the effect of hygienically and effectively drying a reusable ostomy pouch 10, it also prevents potential embarrassment to the patient. Additionally, since the ostomy pouch 10 can be repeatedly used with the present invention, the result is a substantial cost savings and efficiency in this growing segment of the health care industry.

Having described above the presently preferred embodiments of the present invention, it is to be understood that it may be otherwise embodied within the scope of the appended claims.

I claim:
1. An apparatus for drying an ostomy pouch comprising:
   a) a plurality of panels, including a top panel, a bottom panel, a back panel and a pair of side panels, joined together along adjacent outer edges to form a hollow, box-shaped structure, and further including a front panel attached to one of said bottom, top and side panels and moveable from a closed position adjacent said top, bottom and side panels, to an open position providing access to an interior of said box-shaped structure, with at least two of said top, front and side panels having a plurality of perforations therethrough and permitting air to flow to the interior of said box-shaped structure; and
   b) a substantially L-shaped extensor rod positioned within the interior of said box-shaped structure, said extensor rod including a first segment attached to an inner surface of one of said back and side panels and extending substantially horizontally therefrom, said extensor rod further including a second segment attached to said first segment and extending downwardly and vertically toward said bottom panel and having a lower end which is spaced above said bottom panel, said extensor rod further including a raised ridge on an upper surface thereof where the first and second segments are joined together, with said extensor rod configured to receive and hold an ostomy pouch thereon by passing a mouth rim of the ostomy pouch over the lower end of the second segment, along the second segment and over the raised ridge with said mouth rim resting securely on the first segment behind the raised ridge and with the ostomy pouch hanging along and held open by the first segment of said extensor rod and thereby permitting the ostomy pouch to be dried.

2. The apparatus of claim 1 wherein said extensor rod is attached to an inner surface of said back panel.

3. The apparatus of claim 1 wherein each of said top, front and side panels has a plurality of perforations therethrough.

4. The apparatus of claim 1 wherein said second segment of said extensor rod is flexible, cylindrically shaped and includes a lower end which is rounded and smooth.

5. The apparatus of claim 1 wherein said front panel includes a first vertical edge connected by at least one hinge to one of said side panels and a second vertical edge carrying a clasping means for clasping said second vertical edge to the other of said side panels.

6. The apparatus of claim 1 wherein said front panel includes a name plate holder.

7. The apparatus of claim 1 further including a wall mounting bracket on an outer surface of said back panel.

8. The apparatus of claim 1 further including a drip pan carried on an upper surface of the bottom panel and beneath the extensor rod and configured for collecting discharge from an ostomy pouch mounted on said extensor rod.

9. The apparatus of claim 1 wherein said panels and extensor rod are constructed from an inert material which may be sterilized.

10. The apparatus of claim 9 wherein said inert material is selected from the group consisting of polyamide polymers, polycarbonates, styrene-acrylonitrile resins, and polyethersulfones.

11. An apparatus for drying an ostomy pouch comprising:
  a) a plurality of panels, including a top panel, a bottom panel, a back panel and a pair of side panels, joined together along adjacent outer edges to form a hollow, box-shaped structure, and further including a front panel attached to one of said bottom, top and side panels, and moveable from a closed position adjacent said top, bottom and side panels, to an open position providing access to an interior of said box-shaped structure, with each of said top, front and side panels having a plurality of perforations therethrough and permitting air to flow to the interior of said box-shaped structure; and
  b) a substantially L-shaped extensor rod positioned within the interior of said box-shaped structure, said extensor rod including a first segment attached to an inner surface of said back panel and extending substantially horizontally therefrom, said extensor rod further including a flexible second segment attached to said first segment and extending downwardly and vertically toward said bottom panel and having a lower end which is spaced above said bottom panel, said extensor rod further including a raised ridge on an upper surface thereof where the first and second segments are joined together, with said extensor rod configured to receive and hold an ostomy pouch thereon by passing a mouth rim of the ostomy pouch over the lower end of the second segment, along the second segment and over the raised ridge with said mouth rim resting securely on the first segment behind the raised ridge and with the ostomy pouch hanging along and held open by the first segment of said extensor rod and thereby permitting the ostomy pouch to be dried.

12. The apparatus of claim 11 further including a fastening means for fastening said box-shaped structure to a wall.

13. The apparatus of claim 12 wherein said fastening means includes a wall mounting bracket on an outer surface of said back panel and having a slot therein.

14. The apparatus of claim 11 further including a drip pan carried on an upper surface of the bottom panel and beneath the extensor rod and configured for collecting discharge from an ostomy pouch mounted on said extensor rod.

15. The apparatus of claim 11 wherein said panels and extensor rod are constructed from an inert material which may be sterilized.

16. An apparatus for drying an ostomy pouch comprising:
  a) a plurality of panels, including a top panel, a bottom panel, a back panel and a pair of side panels, joined together along adjacent outer edges to form a hollow, box-shaped structure, and further including a front panel connected by at least one hinge along a first vertical edge of said front panel to a front vertical edge of one of said side panels, with said front panel moveable from a closed position adjacent said top, bottom and side panels, in which said front panel is latched by a latching means along a second vertical edge of said front panel to a latch receiving means along a front vertical edge of the other of said side panels, to an open position providing access to an interior of said box-shaped structure, and with each of said top, front and side panels having a plurality of perforations therethrough and permitting air to flow to the interior of said box-shaped structure; and
  b) a substantially L-shaped extensor rod positioned within the interior of said box-shaped structure, said extensor rod including a first segment attached to an inner surface of said back panel and extending substantially horizontally therefrom, said extensor rod further including a flexible second segment attached to said first segment and extending downwardly and vertically toward said bottom panel and having a lower end which is spaced above said bottom panel, said extensor rod further including a raised ridge on an upper surface thereof where the first and second segments are joined together, with said extensor rod configured to receive and hold an ostomy pouch thereon by passing a mouth rim of the ostomy pouch over the lower end of the second segment, along the second segment and over the raised ridge with said mouth rim resting securely on the first segment behind the raised ridge and with the ostomy pouch hanging along and held open by the first segment of said extensor rod and thereby permitting the ostomy pouch to be dried.

17. The apparatus of claim 16 further including a fastening means for fastening said box-shaped structure to a wall.

18. The apparatus of claim 17 wherein said fastening means includes a wall mounting bracket on an outer surface of said back panel and having a slot therein.

19. The apparatus of claim 16 further including a drip pan carried on an upper surface of the bottom panel and beneath the extensor rod and configured for collecting discharge from an ostomy pouch mounted on said extensor rod.

20. The apparatus of claim 16 wherein said panels and extensor rod are constructed from an inert material which may be sterilized.

* * * * *